United States Patent [19]

Yazdi et al.

[11] Patent Number: 6,022,560
[45] Date of Patent: *Feb. 8, 2000

[54] PHARMACEUTICAL COMPOSITIONS, NOVEL USES, AND NOVEL FORM OF α-TOCOPHERYLPHOSPHOCHOLINE

[75] Inventors: Parvin T. Yazdi; Thaddeus P. Pruss, both of Madison, Wis.

[73] Assignee: Clarion Pharmaceuticals Inc., Madison, Wis.

[*] Notice: This patent is subject to a terminal disclaimer.

[21] Appl. No.: 09/093,129

[22] Filed: Jun. 8, 1998

Related U.S. Application Data

[63] Continuation-in-part of application No. 08/703,446, Aug. 27, 1996, Pat. No. 5,763,423.

[51] Int. Cl.[7] .................. A61K 9/127; A61K 31/685; A61K 31/355
[52] U.S. Cl. .................. 424/450; 424/451; 424/464; 424/43; 514/78; 514/458
[58] Field of Search .................. 424/450, 451, 424/464, 1.21, 9.321, 9.51, 417; 516/78, 458; 428/402.2, 43–45, 434, 435

[56] References Cited

U.S. PATENT DOCUMENTS

| | | | |
|---|---|---|---|
| 4,861,580 | 8/1989 | Janoff | 424/1.1 |
| 5,763,423 | 6/1998 | Yazdi | 514/78 |

FOREIGN PATENT DOCUMENTS

| | | |
|---|---|---|
| 1-211578 | 8/1989 | Japan . |

OTHER PUBLICATIONS

Raschke, W.C.; Baird, S.; Ralph, P. and Nakoinz, I., Functional Macrophage Cell Lines Transformed by Abelson Leukemia Virus, *Cell* (1978), 15:261–267.

Cohen et al., Total Synthesis of All Eight Stereoisomers of α–Tocopheryl Acetate. Determination of Their Diastereoisomeric and Enantiomeric Purity by Gas Chromatography, *Helv. Chimica Acta*. (1981), 64:1158–1173.

Chan et al., Synthesis of (2R,4'R,8"R)–α–Tocopheryl Acetate (Vitamin E. Acetate) Using [3,3] Sigmatropic Rearrangement, *J. Org. Chem.* (1978), 43:3435–3440.

Erlich et al., Searching For Antiviral Materials From Microbial Fermentations, *Ann. NY Acad. Sci.* (1965), 130:5–16.

Dean A. Handley, Quantitation of In Vitro and In Vivo Biological Effects of Platelet Activating Factor, *Pharmacological Methods in the Control of Inflammation* (1989), pp. 23–58.

Kiyose et al., *Lipids* (1995), 30(11):1015–1018.

Koltai, M. et al., Platelet Activating Factor (PAF), A Review of its Effects, Antagonists and Possible Future Clinical Implications (Part 1), *Drugs* (1991), 42:9–29.

S.L. Kunkel, "Inflammatory Cytokines", pp. 1–15 in *Manual of Vascular Mediators*, P.A. Ward, Editor.

Ralph, P. and Nakoinz, Ilona, Antibody–Dependent Killing of Erythrocyte and Tumor Targets by Macrophage–Related Cell Lines: Enhancement by PPD and LPS, *J. Immunology* (1977), 119:950–954.

Robeson et al., Isolation of an l–Epimer of Natural d–α–Tocopherol, *J. Am. Chem. Soc.* (1962), 84:3196–3197.

M.A. Trush et al., "The Generation of Chemiluminescence by Phagocytic Cells," *Methods of Enzymology* (1978), 57:462–494.

Ostro in Amer. J. of Hospital Pharmacy. 46, p. 1576 1989.

*Primary Examiner*—Gollamudi S. Kishore
*Attorney, Agent, or Firm*—DeWitt Ross & Stevens S.C.; Salvatore R. Conte, Esq.

[57] ABSTRACT

α-Tocopherylphosphocholine and salts thereof have been discovered to possess antiviral, anti-fungal, anti-inflammatory, PAF-antagonist, and ultra-violet radiation-blocking activities. The compound and salts have also been discovered to be capable of forming liposomes. The present invention thus provides methods of treating viral and fungal infections, inflammatory disorders and pathophysiological conditions due to PAF activity in a mammal by administering to the mammal α-tocopherylphosphocholine or a pharmaceutically acceptable salt thereof. The invention also provides pharmaceutical compositions comprising α-tocopherylphosphocholine or a pharmaceutically acceptable salt thereof and a pharmaceutically acceptable carrier. Further, the invention provides liposomes which comprise α-tocopherylphosphocholine or a salt thereof as a structural component of the liposome bilayer.

9 Claims, No Drawings

PHARMACEUTICAL COMPOSITIONS, NOVEL USES, AND NOVEL FORM OF α-TOCOPHERYLPHOSPHOCHOLINE

This is a Continuation-in-Part of application Ser. No. 08/703,446, filed Aug. 27, 1996 now U.S. Pat. No. 5,763,423.

TECHNICAL FIELD

The present invention relates to novel compositions comprising α-tocopherylphosphocholine and salts thereof and novel methods of using these compounds. The compounds have been discovered to form liposomes and to possess antiviral, anti-fungal, anti-inflammatory, PAF-antagonist, and UV radiation-blocking activities.

BACKGROUND OF THE INVENTION

The ester of α-tocopherol with phosphocholine, α-tocopherylphosphocholine (also known as α-tocopherolphosphocholine), a method of manufacturing same, and pharmaceutically acceptable salts thereof have been described in the literature. See, e.g., Japanese Public Patent Disclosure No. 1-211578, published Aug. 24, 1989.

It has now been found that α-tocopherylphosphocholine, also referred to herein as CPR-2001, and its pharmaceutically acceptable salts (collectively the "subject compounds") are useful chemopreventative and adjuvant agents in several aspects. Further, it has been found that the subject compounds form liposomes.

SUMMARY OF THE INVENTION

The present invention relates to the surprising and unexpected discoveries that the subject compounds are effective to treat, control or prevent viral and fungal infections and inflammation and to antagonize the activities of PAF (platelet-activating factor). The subject compounds are also effective in blocking ultraviolet (UV) radiation, especially UV-B radiation.

The invention also relates to the surprising and unexpected discovery that the subject compounds form liposomes.

More particularly, the invention provides a method of treating a susceptible viral or fungal infection or inflammation or antagonizing PAF-activities in a mammal, which method comprises administering to the mammal an amount of α-tocopherylphosphocholine or a pharmaceutically acceptable salt thereof that is effective to treat the infection or inflammation or antagonize the PAF-activities.

The invention also provides pharmaceutical compositions which comprise an antiviral-effective, antifungal-effective, anti-inflammatory-effective, PAF-activity-antagonizing-effective or UV radiation-blocking amount of α-tocopherylphosphocholine or a pharmaceutically acceptable salt thereof and a pharmaceutically effective carrier.

Further, the invention provides a liposome which comprises α-tocopherylphosphocholine or a salt thereof as a structural component of the bilayer of the liposome. The liposomes of the invention can be employed as vehicles to deliver α-tocopherylphosphocholine or a pharmaceutically acceptable salt thereof in a therapeutic use thereof or as vehicles to deliver other therapeutically active substances carried by the liposomes.

DETAILED DESCRIPTION OF THE INVENTION

The present invention provides a method for treating viral or fungal infections or inflammation in a mammal suffering therefrom by administering to the mammal an antiviral-effective, anti-fungal-effective, or anti-inflammation-effective amount of α-tocopherylphosphocholine or a pharmaceutically acceptable salt thereof.

The present invention also provides a method for antagonizing PAF-activities (and treating the related pathological conditions—such as inflammation or bronchial asthma) in a mammal which comprises administering to the mammal a PAF-activity-antagonizing-effective amount of α-tocopherylphosphocholine or pharmaceutically acceptable salt thereof.

In another aspect, the invention provides pharmaceutical compositions comprising α-tocopherylphosphocholine or a pharmaceutically acceptable salt thereof, i.e., "active ingredient", together with a pharmaceutically acceptable carrier therefor and, optionally, other therapeutically active ingredients. The pharmaceutical compositions of the invention comprise an amount of α-tocopherylphosphocholine or a pharmaceutically acceptable salt thereof that is effective to treat a viral or fungal infection or inflammation in a mammal suffering therefrom, to which the composition is administered, or effective to antagonize PAF-activities (and treat the related pathological conditions) in a mammal, to which the composition is administered, or to block UV radiation (when applied topically). In a pharmaceutical composition of the invention, the carrier must be pharmaceutically acceptable in the sense of being compatible with other ingredients in the particular composition and not deleterious to the recipient thereof. The compositions include those suitable for oral, topical (including compositions suitable for ophthmalogic and nasal administration), rectal or parenteral (including subcutaneous, intramuscular, intradermal and intravenous) administration.

Humans are among the mammals that can be treated by the methods and with the compositions of the invention.

Still another aspect of the present invention is liposomes which comprise α-tocopherylphosphocholine or a salt thereof as a structural component of the bilayer. In this connection, preferred salts are pharmaceutically acceptable salts. A compound in a liposome is a "structural component" of the bilayer of the liposome if the compound, when the only lipophilic or amphophilic substance suspended in an aqueous medium, forms liposomes when the suspension is subjected to liposome-forming conditions. Thus, the invention comprehends liposomes of which the structural components of the bilayer consist essentially (for liposome integrity) of α-tocopheryl-phosphocholine or a salt thereof or comprise α-tocopherylphosphocholine or a salt thereof together with other compounds which are also structural components. The liposomes of the invention may comprise, in the bilayer or the non-bilayer (e.g., aqueous) compartment, compounds that are not "structural components" as defined herein. Such compounds, which are not structural components, may be therapeutically active. Thus, the liposomes of the invention are useful as carriers for delivery of not only α-tocopherylphosphocholine or a pharmaceutically acceptable salt thereof but also other therapeutically active compounds.

α-tocopherylphosphocholine is represented by the general Formula (I):

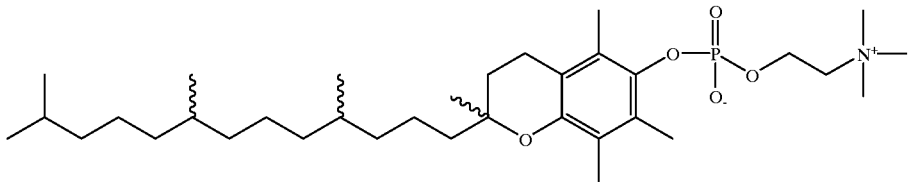

The skilled will immediately recognize that α-tocopherylphosphocholine shown in Figure (I) has three asymmetric carbon atoms in its structure and, consequently, has 8 stereoisomers (4 pairs of enantiomers). The compound as used in accordance with the present invention may be one or a mixture of two or more of the biologically-active stereoisomers. Each of the stereoisomers is biologically active. See, for example, Kiyose et al. (1995) *Lipids* 30(11) :1015–1018. The invention encompasses use of all of the stereoisomers of the compound of Formula (I), as well as the pharmaceutically acceptable salts of the compounds (including the stereoisomers) of Formula (I). Unless specifically qualified otherwise, reference herein to "compound of Formula (I)" or to "α-tocopherylphosphocholine" means any combination of the stereoisomers.

A substantially pure stereoisomer may be obtained, substantially free of the other 7 stereoisomers, by the application of art-known resolution methodology such as, for example, chromatography using chiral columns or using in the preparation stereoisomerically appropriate precursors. It is noteworthy that α-tocopherol as it occurs in nature and can readily be obtained from natural sources, and which is commonly referred to as d-α-tocopherol, is the substantially pure 2R,4'R,8'R stereoisomer (the one with the R configuration at all of the asymmetric centers, employing the standard Cahn-Ingold-Prelog system for designating configurations). Cohen et al., *Helv. Chim. Acta* 64, 1158–1173 (1981). Further, methods for preparing in substantially pure form each of the 8 stereoisomers of α-tocopherol are known. See, for example, Cohen et al., supra; Chan et al., *J. Org. Chem.* 43, 3435–3440 (1978); Robeson et al., *J. Am. Chem. Soc.* 84, 3196–3197 (1962).

Preparation of α-tocopherylphosphocholine can be carried out by art-recognized procedures, beginning with α-tocopherol. See, for example, Japanese Public Patent Disclosure No. 1-211578, published Aug. 24, 1989.

The compound of Formula (I), as a substantially equimolar mixture of the 8 stereoisomers, can be prepared from commercially available, synthetic α-tocopherol, so-called "d,l-α-tocopherol," as a starting material. This d,l-α-tocopherol is a substantially equimolar mixture of the 8 stereoisomers of α-tocopherol.

The salts of α-tocopherylphosphocholine, the therapeutic use of which is within the scope of the invention, are pharmaceutically acceptable salts and include acid addition salts, for example, those made with hydrochloric, hydrobromic, hydroiodic, nitric, sulfuric, phosphoric, carbonic, acetic, citric or lactic acids, as well as salts made with bases, such as, for example, sodium hydroxide, potassium hydroxide or calcium hydroxide. The salts of the invention are made by conventional means well known to those of ordinary skill in the art.

UTILITY

The compound of Formula (I) and the pharmaceutically acceptable salts thereof are used in accordance with the invention as chemopreventative and adjuvant agents in several aspects, as presently described. For each indication, the compound of Formula (I) and salts thereof may be used alone or in combination with other compatible medicaments.

A. Antiviral:

α-tocopherylphosphocholine and its pharmaceutically acceptable salts possess antiviral activity and can be used in the control or prevention of viral infections, e.g., of herpes simplex and polio viral infections. For illustrative purposes, the in vitro activity of the compound CPR-2001 in inhibiting Herpes simplex virus type-1 and Poliovirus type III is demonstrated in the assays illustrated in Examples 1A and 1B.

The first assay is for inhibition of cytopathic effects (CPE) caused by viral-infection of the cells and the second is a standard viral yield reduction assay. This yield reduction assay is a modification of the general method described by Erlich et al., *Ann. NY Acad. Sci.* 130, 5–16 (1965). The two assays demonstrate the marked antiviral activity of compound CPR-2001. No apparent cytotoxicity at antivirally effective levels has been observed.

CPR-2001 and its pharmaceutically acceptable salts are effective particularly for the treatment of an infection by Herpes viruses (particularly Herpes simplex, including its two immunological types, HSV-1 and HSV-2), and Poliovirus (all immunological variants), although infections caused by other viruses, such as, for example, Varicella-zoster virus, Togaviruses, Cytomegalovirus (CMV), Epstein-Barr virus (EBV), Picornaviruses, Rhinovirus, Human papilloma viruses and Hepatitis viruses, among others, may also be effectively treated.

This invention thus provides a method of treating a host mammal having a susceptible viral infection comprising administering to said mammal an antiviral effective amount of α-tocopherylphosphocholine or a pharmaceutically acceptable salt thereof. The invention also provides pharmaceutical compositions comprising an antiviral-effective amount of α-tocopherylphosphocholine or a pharmaceutically acceptable salt thereof and a pharmaceutically acceptable carrier.

B. Anti-Fungal:

α-tocopherylphosphocholine and its pharmaceutically acceptable salts possess antifungal activity and can be used in the control or prevention of fungal infections. This is illustrated by the in vitro activity of CPR-2001 in inhibiting *Candida albicans* and *Cryptococcus neoformans*, as demonstrated by the assay and results of Example 2.

In addition to *C. albicans* and *C. neoformans*, infections caused by other fungi, such as, for example, Aspergillus, Rhizopus, Dermatophytes and Histoplasma spp., among others, may also be effectively treated.

The subject invention thus provides a method of treating a host mammal having a susceptible fungal infection which comprises the administration to said mammal of an antifungal effective amount of α-tocopherylphosphocholine or a pharmaceutically acceptable salt thereof. The invention also provides pharmaceutical compositions comprising an antifungal-effective amount of α-tocopherylphosphocholine or a pharmaceutically acceptable salt thereof and a pharmaceutically acceptable carrier.

C. Anti-Inflammatory:

Inflammation is a complex process, involving a variety of cell types including macrophages. See, for example, S. L. Kunkel, "Inflammatory Cytokines", pp. 1–15, in Manual of Vascular Mediators, P. A. Ward, Editor, produced by the publishers of Hospital Practice. References relative to macrophages are numerous, including, for example, *J. Immunology* 119, 950–954 (1977) and *Cell* 15, 261–267 (1978).

Macrophages are activated by injection and by a wide variety of non-infectious irritants and proinflammatory agents. Upon activation, macrophages participate in a variety of reactions. They may phagocytize bacteria and kill them by either oxygen-dependent or oxygen-independent pathways. They are activated to increase oxygen consumption and production of reactive oxygen species (for example, superoxide). In addition, they release a variety of inflammatory cytokines, including several interleukins and tumor necrosis factor (TNF-0). Inhibition of any of these pathways can lead to reduced inflammation.

The RAW 264.7 cell line (ATCC TIB 71) is a murine monocyte/macrophage line that shows many of the differentiative functions of a macrophage. The cells are capable of phagocytosis and undergo an oxidative burst in response to appropriate signals. Agents that inhibit the activation of these cells in vitro are therefore inhibitors of critical steps in inflammatory processes.

Activation of macrophages and other phagocytic cell types initiates a cascade of actions that include increased oxygen consumption (respiratory burst) and production of oxygen radicals. These events can be measured in a variety of ways, including chemiluminescence based on the addition of luminol (see M. A. Trush et al., "The Generation of Chemiluminescence by Phagocytic Cells," *Methods in Enzymology* 57, 462–494 (1978)). Because chemiluminescence is induced by the increased production of oxygen radicals that are thought to be important in intracellular killing of bacteria, chemiluminescence has long been used as an index of phagocytic cell activity. In addition, oxygen radical production is associated with inflammatory responses and may have adverse consequences in noninfectious inflammation. For this reason, macrophage activation is of critical importance in studies of the inflammatory process. Agents that reduce macrophage activation are likely to have utility as anti-inflammatory agents. Since luminescence generated from luminol is a recognized marker of macrophage activation, the finding that the subject compounds strongly inhibit chemiluminescence in macrophages correlates to their usefulness in ameliorating inflammation.

As shown in the chemiluminescence (CL) assay of Example 3, CPR-2001 exhibits marked dose-related anti-inflammatory activity. CPR-2001 and its pharmaceutically acceptable salts may thus be utilized for ameliorating inflammatory conditions such as, for example, rheumatoid arthritis, osteoarthritis, acute bursitis, tendinitis and allied inflammatory disorders.

It has also been found that medicinal agents which cause inflammation as an unintended side-effect can be encapsulated in liposomes of CPR 2001 whereby the inflammatory side-effect is reduced without adversely affecting the desired biological activity of the encapsulated reagent. As described in the Examples, in an in vivo model of inflammation (PMA-induced ear edema in mice) the inflammation caused by medicinal compounds such as retinoic acid and 5-fluorouracil can be significantly reduced by incorporating these compounds into liposomes wherein CPR 2001 is a structural component of the liposome. Medicinal agents of any description can be encapsulated within such liposomes.

The instant invention thus provides a method of treating a host mammal afflicted with an inflammatory disorder comprising administering to said mammal an anti-inflammatory effective amount of α-tocopherylphosphocholine or a pharmaceutically acceptable salt thereof. The invention also provides a method of ameliorating inflammatory side-effects of pharmaceutical compounds by incorporating the compounds into a liposome wherein CPR 2001 is a structural component of the liposome. The invention also provides pharmaceutical compositions comprising an anti-inflammatory-effective amount of a-tocopherylphosphocholine or a pharmaceutically acceptable salt thereof and a pharmaceutically acceptable carrier.

D. PAF-Antagonism:

Platelet-activating factor (PAF, 1-O-$C_{16-18}$alkyl-2(R) acetyl-sn-glyceryl-3-phosphocholine), its effect on platelets and its biological effects have been the subject of many reported studies since its discovery in the early 1970's. Typical PAF literature reviews include those of Dean A. Handley, Pharmacological Methods in the Control of Inflammation, pp. 23–58, 1989, and Matyas Koltai et al., *Drugs* 42, 9–29 (1991).

PAF has been shown to be a mediator of inflammation and has been found in lung fluids of asthma patients. It is a chemoattractant and encourages the migration of neutrophils and eosinophils to sites of inflammation and to the airways of asthmatic patients. Moreover, PAF has been shown to be a powerful bronchoconstrictor of the airways of asthmatic patients. In addition PAF has been found in the psoriatic lesions of psoriasis patients. Accordingly, antagonists of PAF have potential utility in treating inflammatory states including rheumatoid arthritis, asthma and psoriasis, and immediate and delayed type hypersensitivity reactions.

The understanding of PAF has been markedly advanced by the development and availability of PAF antagonists and their clinical implications. As noted in Handley, supra., page 45, there are intense and focused studies on PAF, and a prominent pharmaceutical effort to develop antagonists, with clinical trials of PAF antagonists in man in progress.

It has now been found that α-tocopherylphosphocholine and its pharmaceutically acceptable salts possess marked PAF antagonist activity. Example 4 hereafter demonstrates the inhibition of the constrictor activity of PAF on the test animal airway. The subject compounds are thus useful in ameliorating PAF-related disease states, including PAF-induced bronchial asthma.

The subject invention thus provides a method of inhibiting PAF activity in a host mammal having a susceptible PAF-induced pathophysiological condition which comprises the administration to said mammal of a PAF-antagonist effective amount of α-tocopherylphosphocholine or a pharmaceutically acceptable salt thereof. The invention also provides pharmaceutical compositions comprising a PAF-antagonist-effective amount of α-tocopherylphosphocholine or a pharmaceutically acceptable salt thereof and a pharmaceutically acceptable carrier.

E. Ultra-violet (UV) Radiation Blocker:

When an electron in a molecule is promoted to a higher energy level, the absorption of UV or visible radiation occurs. As a consequence, the electronic structure of a molecule governs both the efficiency and electromagnetic frequency of the absorption. Usually, conjugated double bonds are the key feature of molecules which are effective UV-absorbers (i.e., blockers). Molecules which lack conjugated double bonds rarely absorb in the UV-A region (320 to 400 nm) or UV-B region (280–320) of the spectrum. It must also be noted, however, that not all molecules which contain conjugated double bonds are effective absorbers in these regions of the spectrum.

Compounds which efficiently absorb radiation in either or both of the UV-A and UV-B regions are useful in sunscreen and other dermatological products, including make-up, because they block the damaging effects sun exposure has on the skin.

To evaluate the UV-blocking properties of the subject compounds, a 1.0 mM solution of CPR 2001 was prepared in 2-propanol at room temperature. The UV-visible spectrum was then recorded using a conventional spectrophotometer. (A Hewlett-Packard Scanning UV-Visible spectrophotometer was used.) CPR 2001 shows a marked absorption in the UV-B region, the absorption stretching from about 270 nm to about 310 nm and having a maximum absorption at about 295 nm.

Because the electronic structure of all of the subject compounds are essentially identical, they are expected to exhibit virtually identical absorption patterns in the UV region.

Thus, the invention includes a pharmaceutical composition for blocking UV radiation, the composition comprising one or more of the subject compounds in combination with a pharmaceutically-suitable carrier, preferably a carrier suitable for topical application to the skin, lips, or hair.

PHARMACEUTICAL COMPOSITIONS

As indicated above, the invention also entails pharmaceutical compositions comprising α-tocopherylphosphocholine or a pharmaceutically acceptable salt thereof together with a pharmaceutically acceptable carrier therefor and, optionally, other therapeutically active substances in addition to the α-tocopherylphosphocholine or salt thereof. The pharmaceutical compositions of the invention comprise an amount of α-tocopherylphosphocholine or a pharmaceutically acceptable salt thereof that is effective to treat a viral or fungal infection or inflammation in a mammal suffering therefrom, to which the composition is administered, or effective to antagonize PAF-activities (and treat the related pathological conditions) in a mammal, to which the composition is administered. In a pharmaceutical composition of the invention, the carrier must be pharmaceutically acceptable in the sense of being compatible with other ingredients in the particular composition and not deleterious to the recipient thereof. The compositions include those suitable for oral, topical, rectal or parenteral (including subcutaneous, intramuscular, intradermal and intravenous) administration.

In a particular aspect, the pharmaceutical compositions comprise the active ingredient (α-tocopherylphosphocholine or pharmaceutically acceptable salt thereof) presented in unit dosage form. The term "unit dosage" or "unit dose" is denoted to mean a predetermined amount of the active ingredient sufficient to be effective for treating each of the indicated activities. Preferred unit dosage formulations are those containing a daily dose, daily sub-dose, or an appropriate fraction thereof, of the administered active ingredient.

The pharmaceutical compositions may be prepared by any of the methods well known in the art of pharmacy. All methods include the step of bringing the active ingredient into association with a carrier which constitutes one or more accessory ingredients. In general, the compositions are prepared by uniformly and intimately bringing the active ingredient into association with a liquid or solid carrier and then, if necessary, shaping the product into the desired unit dosage form.

Compositions of the present invention suitable for oral administration may be presented as discrete unit dosages, e.g., as capsules, cachets, tablets, boluses, lozenges and the like, each containing a predetermined amount of the active ingredient; as a powder or granules; or in liquid form, e.g., as a collyrium, suspension, solution, syrup, elixir, emulsion, dispersion and the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients or excipients, e.g., binders, lubricants, inert diluents, surface active or dispersing agents. Molded tablets may be made by molding in a suitable machine, a mixture of the powdered active compound with any suitable carrier.

Compositions suitable for parenteral administration conveniently comprise a sterile injectable preparation of the active ingredient in, for example, a solution which is preferably isotonic with the blood of the recipient. Useful formulations also comprise concentrated solutions or solids containing the active ingredient which upon dilution with an appropriate solvent give a solution suitable for parenteral administration. The parenteral compositions include aqueous and non-aqueous formulations which may contain conventional adjuvants such as buffers, bacteriostats, sugars, thickening agents and the like. The compositions may be presented in unit dose or multi-dose containers, for example, sealed ampules and vials.

Compositions suitable for topical or local application (including ophthamological administration) comprise the active ingredient formulated into pharmaceutically-acceptable topical vehicles by conventional methodologies. Common formulations include drops, collyriums, aerosol sprays, lotions, gels, ointments, plasters, shampoos, transferosomes, liposomes and the like.

Compositions suitable for inhalation administration, for example, for treating bronchial asthma, wherein the carrier is a solid, include a micronized powder or liquid formulation having a particle size in the range of from about 5 microns or less to about 500 microns, for rapid inhalation through the nasal or oral passage from a conventional inhalation squeeze or spray container. Suitable liquid nasal compositions include conventional nasal sprays, nasal drops and the like, of aqueous solutions of the active ingredient and optional adjuvants.

As explained in more detail below, the active ingredient may be provided in the form of a liposome.

In addition to the aforementioned ingredients, the compositions of this invention may further include one or more optional accessory ingredients(s) utilized in the art of pharmaceutical formulations, e.g., diluents, buffers, flavoring agents, colorants, binders, surfactants, thickeners, lubricants, suspending agents, preservatives (including antioxidants) and the like.

The amount of active ingredient required to be effective for each of the indicated activities will, of course, vary with the individual mammal being treated and is ultimately at the discretion of the medical or veterinary practitioner. The factors to be considered include the species and sex of the mammal, the condition being treated, the route of administration, the nature of the formulation, the mammal's body weight, surface area, age and general condition, and the particular compound to be administered.

In general, the pharmaceutical compositions of this invention contain from about 0.5 to about 500 mg and, preferably, from about 5 to about 350 mg of the active ingredient, preferably in a unit dosage form, for each of the indicated activities. However, a suitable effective dose is in the range of about 0.1 to about 200 mg/kg body weight per day, preferably in the range of about 1 to about 100 mg/kg per day, calculated as the non-salt form of α-tocopherylphosphocholine. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

For example, for a 75 kg mammal, a dose range would be about 7.5 to about 1500 mg per day, and a typical dose would be about 800 mg per day. If discrete multiple doses are indicated, treatment might typically be 200 mg of a compound of Formula (I) given 4 times per day.

In topical formulations, the subject compounds are preferably utilized at concentrations of from about 0.1% to about 5.0% by weight.

LIPOSOMES

As also indicated above, still another aspect of the present invention is α-tocopherylphosphocholine or a pharmaceutically acceptable salt thereof in the novel physical form of a liposome (i.e., as a structural component of the bilayer of the liposome).

Liposomes, which are microscopic, man-made spheres of fatty material, were first formed from phospholipids. Although it has been known for a long time that other lipids, such as cholesterol, dicetyl phosphate, and stearylamine can be incorporated into liposome membranes (i.e., liposome bilayers) that contain phospholipids, only phospholipids were known to be "structural components" of the membranes, i.e., to form liposomes when suspended in aqueous media without any other lipophilic or amphophilic substance. Subsequently, it was found that certain ammonium salts could also form liposomes. In particular, dialkyl dimethyl ammonium salts will form liposomes if the alkyl chains are 12 carbons or longer. More recently, there have been developed a series of novel structures, based on the chemical structure of phospholipids, that also form liposomes. In addition, much information has been gained on the type of chemical structure necessary for liposome formation (i.e., to be a structural component of a liposome bilayer). Usually, the liposome-forming molecule must be one with two alkyl chains and a polar headgroup, although there are some exceptions to this rule. For example, fatty acids, which have only a single alkyl chain, will form liposome structures under conditions where they dimerize through hydrogen-bonding.

The structure of α-tocopherylphosphocholine does not suggest that it, or a salt thereof, would be capable of forming a liposome when suspended alone (i.e., without another lipophilic or amphophilic compound) in an aqueous medium subjected to liposome-forming conditions. α-tocopherylphosphocholine has only a single alkyl-like moiety, namely the tocopheryl group, connected to a phosphocholine group. Molecules of this type usually form micelles. However, without intending to be bound herein by theory, the ability, first disclosed in this application, of α-tocopherylphosphocholine to form a liposome might be explained retrospectively by the bulky nature of the tocopheryl group, which in molecular terms might be functionally equivalent to a dialkyl structure containing only straight hydrocarbon chains. Even this consideration, however, would not lead to a prediction that α-tocopherylphosphocholine or a salt thereof would form a liposome. It might form a number of more complex micellar structures, or might not even suspend at all appropriately for liposome formation in an aqueous medium. Therefore, the capacity of α-tocopherylphosphocholine and salts thereof to form a liposome by themselves (i.e., to be structural components in the bilayers of liposomes) is a surprising and unexpected observation that could not have been predicted until the observation had been made. Example 6 hereafter details the preparation of the subject liposomes of the invention.

This novel liposome form of α-tocopherylphosphocholine or a salt (preferably pharmaceutically acceptable salt) thereof has beneficial pharmaceutical applications. For example, it advantageously may be incorporated into topical pharmaceutical compositions of the subject compounds such as ointments, salves, creams and creamy liquids, dispersions and the like. The subject liposomes are also suitable for transdermal application of other therapeutic agents by enhancing the absorption of such agents through the skin of humans and animals. As with other known liposomes, such agents would be encapsulated within the internal aqueous compartment of the liposome structure.

In addition to encapsulation of drugs within the internal aqueous space, liposomes may also be prepared from mixtures of the subject compounds with other amphophilic therapeutic agents, such as, for example, phospholipids, cholesterol and certain drugs such as Amphotericin B and Doxorubicin. The preparation strategy would require the mixing of the subject compound with the other component in an organic solvent. This initial mixing would then be followed, for example, by evaporation of the solvent to give a mixed film of the components. This film would then be swollen in aqueous medium as described in Example 6.

Other techniques known in the art could be employed to make liposomes with α-tocopherylphosphocholine or salts thereof. These include the reverse phase evaporation method, the dehydration-rehydration method, and solvent injection methods. Liposome formation with α-tocopherylphosphocholine and salts thereof would also respond to known size-control methods in addition to sonification. Principal among these is the method of extrusion through polycarbonate membranes, or on an industrial scale, filtration with ceramic filters.

The liposomes can also be used to encapsulate medicinal compounds displaying inflammatory side-effects, thereby mitigating the unwanted inflammatory activity. Encapsulating such compounds within liposomes comprising the subject compounds as structural components of the liposomes diminishes inflammatory side-effects.

The subject invention thus provides α-tocopherylphosphocholine or a salt thereof in the form of a liposome and provides liposomes which comprise this compound or a salt thereof as a structural component of the bilayer (membrane). The invention also provides pharmaceutical compositions comprising said liposome in an effective amount for each of the indicated activities and a pharmaceutically effective carrier, particularly for topical application, as well as such pharmaceutical compositions wherein the α-tocopherylphosphocholine liposome contains another drug encapsulated within the liposome's structure.

The following examples are illustrative only and are included solely to aid in a more complete understanding of the invention disclosed and claimed herein. The Examples do not limit the scope of the present invention in any fashion.

EXAMPLE 1A

Antiviral

Antiviral Assay: Herpes Simplex Virus Type 1

1. Buffalo Green Monkey Kidney cells, obtained from Dr. G. Sedmak, City of Milwaukee, Public Health Department Virology Laboratory, are plated at a density of 7×104 cells per well in a standard flat bottom 96 well cell culture plate. The cells are contained in a volume of 200 µl Dulbecco's Modified Eagles Medium (DMEM) containing 10% serum [1:1 mixture of fetal bovine serum and defined supplemented calf serum (Hyclone, Inc., Ogden, Utah), 10 mM HEPES buffer (pH 7.2), 100 U/ml penicillin and 100 µg/ml streptomycin sulfate]. HEPES and antibiotics are obtained from Sigma Chemical Co. (St.Louis, Mo.). Two wells are plated for each of the following samples: compound CPR-2001, cell control (cells only), virus control (cells infected but not treated), vehicle control (solvent for compound, 9:1 dimethylsulfoxide:ethanol), and cell counts.
2. The cultures are incubated at 37° C. with 5% $CO_2$ until a monolayer of cells is formed on the bottom of each well (usually overnight).
3. The media is removed from the wells by aspiration. The cells are refed with media containing the desired concentration of test compound CPR-2001 (100 µM final concentration), media only (cell control and virus control samples), or solvent (9:1, DMSO:ethanol) at a final concentration of 0.33%. Compound CPR-2001 is dissolved at a stock concentration of 30 mM and diluted 300-fold. The cell count wells receive media only.
4. The cultures are incubated for 24 hr at 37° C. with 5% $CO_2$.
5. At the end of 24 hr, each well is scored for the presence of toxicity (cells exposed to compound but not infected) as indicated by rounding and/or detachment of the cells from the plate. Scoring is as follows: 1+, ≦25% of cells rounded; 2+, 25 to 50% of cells rounded; 3+, 75% of cells rounded; 4+, 100% of cells rounded.
6. The media is removed from the cell count wells by aspiration. The monolayer is rinsed 2× with 100 µl of trypsin:EDTA solution and is incubated at 37° C. until the cells can be suspended (usually 2–5 minutes). The cells are counted in a hemocytometer to determine the number of cells per well.
7. The remaining wells, except the cell control samples, are infected with 2 plaque forming units per cell of the standard HSV-1 KOS strain of virus using the following procedure. The media is aspirated from the wells. Media (50 µl) with 2% serum containing the desired amount of virus is added to each well. The cultures are then incubated at 37° C. with 5% $CO_2$ for 60 minutes. The plate is gently shaken at 15 to 30 minute intervals to insure adequate distribution of the virus and the cells are exposed to the virus. At the end of the incubation period, the excess viral solution is removed by aspiration and the cells are refed (200 µl/well) with media containing 2% serum (cell control and virus control samples), media containing 2% serum and compound CPR-2001, or media containing the vehicle (solvent control) at the same concentration in the test compound wells.
8. The plate is incubated at 37° C. with 5% $CO_2$ for 48 hr.
9. At the end of 48 hr, each well is scored for the presence of CPE as indicated by rounding and/or detachment of the cells from the plate. Scoring is as follows: 1+, ≦25% of cells rounded; 2+, 25 to 50% of cells rounded; 3+, 50 to 75% of cells rounded; 4+, 100% of cells rounded.
10. After scoring for viral CPE, the yield of infectious virus in each well is measured by standard plaque assay on Vero cells (ATCC #CCL81). Virus is released from the cells by freezing and thawing (−80° C. and 37° C.) three times. Serial 10-fold dilutions of each sample are made in media containing 2% serum. Vero cell monolayers of Buffalo Green cells in 6 well cell culture plates (1×10⁶ cells/well) are infected with 100 µl of each dilution (separate well per dilution). Following a 1 hr adsorption period with gentle rocking at 37° C., the virus inoculum is removed, the monolayer is overlaid with 2 ml of 2% methylcellulose in media with 2% serum followed by 2 ml of media with 2% serum. The titer plates are incubated at 37° C. with 5% $CO_2$ until viral plaques become visible (3–4 days). The cells are fixed by adding 2 ml of phosphate buffered saline (PBS) containing 10% (v:v) formalin. The methylcellulose, media and formalin are removed by aspiration. Two mls of PBS-formalin are added and incubated 5 minutes. The fixative is removed and the cells stained with 1% crystal violet in 70% ethanol water (v:v). Excess stain is rinsed from the cells, the number of plaques are counted and the yield of virus in the original sample is calculated.

Results:

Table 1A shows the results of the CPE inhibition assay. Exposure of the cells to compound CPR-2001 markedly inhibits the development of viral cytopathic effect and is not toxic. The DMSO vehicle used for dissolving the compound is not toxic and does not prevent the development of viral CPE, indicating the vehicle has no antiviral activity. The cell control and virus controls also give the expected results. Table 1A also shows the data from the yield reduction assay. As expected, the DMSO (vehicle control) has no effect on viral yield (1×10⁶ pfu/ml) compared to the virus control (1×10⁶ pfu/ml). In contrast, treatment of the cells with compound CPR-2001 reduces the yield to 5.5×10⁴. This represents an 18-fold reduction in infectious virus compared to the virus and vehicle control samples and represents a substantial antiviral effect.

TABLE 1A

ANTI-HERPES SIMPLEX VIRUS ACTIVITY OF COMPOUND CPR-2001

| Sample | Toxicity | Viral CPE | Virus Yields (48 Hours) | | |
|---|---|---|---|---|---|
| | | | PFU/ml | Yield | Reduction[c] |
| Cell Control | N[a] | —[b] | — | — | — |
| Vehicle Control (DMSO/Ethanol) | N | 4+ | 1 × 10⁶ | 1.00 | 0 |
| Virus Control | — | 4+ | 1 × 10⁶ | 1.00 | 0 |
| CPR-2001 | N-± | 1+ | 5.5 × 10⁴ | 0.0555 | 18 |

[a]Not toxic
[b]Not scored
[c]Fold-reduction

EXAMPLE 1B

Antiviral

Antiviral Assay: Poliovirus Type III

The antiviral effect against Poliovirus Type III is demonstrated in similar assays by following the foregoing steps 1 through 10 of Example 1A except for step 7 which is substituted with the following:

7. The cells are then infected. For this study, the Poliovirus Type III vaccine strain is obtained from Dr. G. Sedmak, City of Milwaukee, Public Health Department Virology Laboratory. The cells are infected as follows. The medium is aspirated and replaced with 50 $\mu$l of medium (2% serum) containing 100 TCID50 doses of Poliovirus Type III. The cultures are then incubated at 37° C. with 5% $CO_2$ for 60 minutes. The plate is shaken gently at 15 minute intervals to insure adequate distribution of the virus and the cells are exposed to the virus. At the end of the incubation period, the media containing virus is removed by aspiration and replaced with 200 $\mu$l of media containing compound CPR-2001 (100 $\mu$M), or media only (virus control and vehicle control wells). The cell control wells received media only (no virus).

Results:

Table IB shows the results of the CPE inhibition assay. Exposure of the cells to compound CPR-2001 inhibits the development of viral CPE compared to the virus control and vehicle control samples. The cell control and virus control samples give the expected results. Table 1B also shows the data from the yield reduction assay. Compound CPR-2001 reduces the yield of infectious virus by 10.7-fold compared to the virus control, which represents a substantial antiviral effect.

TABLE 1B

ACTIVITY OF COMPOUND CPR-2001 AGAINST POLIOVIRUS TYPE III

| Sample | Toxicity 24 hr | CPE | Titer | Fold-Reduction |
|---|---|---|---|---|
| Cell Control | N[a] | —[b] | — | — |
| Virus Control | N | 4+ | $2.9 \times 10^7$ pfu/ml | — |
| Vehicle Control | N | 4+ | ND[c] | ND |
| CPR-2001 | N | 2+ | $2.7 \times 10^6$ pfu/ml | 10.7 |

[a]Not toxic
[b]Not scored
[c]ND = not determined

EXAMPLE 2

Antifungal

Assay Protocol:

1. $10^4$ Cells (either *C. albicans* or *C. neoformans*) are placed in wells of a 96-well plate within a total volume of 90 $\mu$l. Cells are grown in RPMI-1640 plus 10% FCS.
2. Add 10 $\mu$l of control or drug to be evaluated (CPR-2001): media; ethanol (0.1%, 1.0% or 10%); Fungizone (2.5 $\mu$g/ml and 5.0 $\mu$g/ml); and CPR-2001 (1 $\mu$g/ml, 10 $\mu$g/ml and 100 $\mu$g/ml).
3. Incubate for 48 hours at 37° C.
4. Remove 100 $\mu$l and dilute 1:8, 1:80 and 1:800;
5. Plate onto Sabourand plates and incubate overnight at 37° C.; and
6. Count and record colonies.

All samples are tested in duplicate in two separate experiments. The data are then averaged to obtain the following results in Table 2. With increasing concentration of CPR-2001, from 1 to 100 $\mu$g/ml, the percent of fungal inhibition also increases.

TABLE 2

ANTIFUNGAL ACTIVITY OF CPR-2001

| | Concentration mcg/ml | % Inhibition |
|---|---|---|
| *Candida albicans* | 1 | 25 |
| | 10 | 40 |
| | 100 | 76 |
| *Cryptococcus neoformans* | 1 | 10 |
| | 10 | 40 |
| | 100 | 73 |

EXAMPLE 3A

Anti-Inflammatory

Chemiluminescence (CL) Assay:

1. Cell line: RAW 264.7 (ATCC TIB 71);
2. Culture medium: DMEM with 10% FBS (attachment dependent);
3. Standard protocol for culturing cell lines: in T-75 or T-150 flasks; 37° C.; 95% air, 5% $CO_2$; 100% humidity;
4. Cell lines are passaged when approximately 80% confluent; with trypsin (1 mg/ml) and EDTA (1 ml EDTA in Ca—Mg free Hank's balanced salt solution); at a 1:4 to 1:5 split;
5. Trypsinize the cells and count with a hemocytometer;
6. Adjust concentration of cells to approximately 1,000,000 cells per ml;
7. Suspend cells in DMEM lacking phenol red and without FBS;
8. Pipette 1 ml into a standard luminometer cuvet (12×75), commercially obtainable from Analytical Luminescence Laboratories, San Diego;
9. Add luminol to final concentration of 1 $\mu$l;
10. Add test compound (0, 1, 3, 10, 30 $\mu$M);
11. Add 100 nanograms of phorbol myristate acetate (PMA);
12. Wait 1 minute and read photo counts (i.e., luminescence) on a Monolight 2010 luminometer available from Analytical Luminescence Laboratories, San Diego;
13. The decrease in measured luminescence as percent of control (no test compound present) is observed by the compound tested at concentrations of 1, 3, 10 and 30 $\mu$M. The results are represented in Table 3 which tabulates the percent inhibition of macrophage activation by the PMA. For comparative purposes, the percent inhibition of α-tocopherol and retinoic acid at the same dosage levels are also indicated.

TABLE 3A

INHIBITION OF MACROPHAGE ACTIVATION BY PMA

| Concentration ($\mu$M | α-Tocopherol | Retinoic Acid | CPR-2001 |
|---|---|---|---|
| 30 | −14 | 6 | 56 |
| 10 | −6 | 3 | 31 |
| 3 | −6 | 6 | 13 |
| 1 | −3 | 2 | 5 |

TABLE 3A-continued

INHIBITION OF MACROPHAGE ACTIVATION BY PMA

| Concentration ($\mu$M) | α-Tocopherol | Retinoic Acid | CPR-2001 |
|---|---|---|---|

Results:
With increasing concentration of CPR-2001, from 1 to 30 $\mu$M, anti-inflammatory activity markedly increases, in contrast to α-tocopherol and retinoic acid.

EXAMPLE 3B

Anti-Inflammatory

Assay: Inhibition of PMA-Induced Ear Inflammation:

A common in vivo model for the evaluation of anti-inflammatory agents is PMA-induced inflammation in mouse ears. This method is described in "Pharmacological Methods in the Control of Inflammation", Joseph Y. Chang and Alan J. Lewis (eds), Alan R. Liss, Inc., N.Y., pp 221–223. In this assay, edema, which is a characteristic of inflammation, is quantified by determining ear thickness or ear weight approximately 6 hours after applying PMA to the ear.

1. Mice: Male CD-1, 21–24 g (Product Number 3002) obtainable from Harlan Sprague Sawley, Indianapolis, Ind., USA;
2. Methodology:
   a. Prepare 0.01% (w.v) PMA in a mixture of equal volumes of acetone and ethanol;
   b. Prepare 0.01% (w/v) PMA and 5% (w.v) test compound in a mixture of equal volumes of acetone and ethanol;
   c. Divide 9 mice into 3 groups of 3 mice each;
   d. Leave one group of mice untreated;
   e. Treat the second group of mice by applying 20 $\mu$L of PMA solution to both ears using a micropipetter;
   f. Treat the third group of mice by applying 20 $\mu$L of PMA solution to the right ear and 20 $\mu$L of PMA/test compound solution to the left ear;
   g. Wait 6 hours and euthanize the mice in a $CO_2$ chamber;
   h. Cut the ears and punch out circles of 6-mm diameter; and
   i. Measure the weight of three appropriate ear punches in the same group together.

The above protocol was used to test CPR 2001 alone and CPR 2001 in combination with various other agents, wherein the other agents were encapsulated within liposomes of CPR 2001.

In a first set of experiments, separate groups of PMA-induced mice were treated with vehicle alone, a 1% solution of dexamethasone, a 5% solution of CPR 2001, a 1% solution of retinoic acid, and a liposome formulation wherein retinic acid was incorporated within CPR 2001 liposomes. The concentration of the liposome formulation was equivalent to 5% CPR 2001 and 1% retinoic acid overall. The percent increase in each of these groups was as follows:

TABLE 3B

|  | % increase in ear weight |
|---|---|
| Vehicle only | 92 |
| 1% Dexamethasone | 18 |
| 5% CPR 2001 | 59 |
| 1% Retinoic Acid (RA) | 151 |
| CPR 2001 + RA | 21 |

Retinoic acid is used topically to treat acne, especially inflammatory acne. An increase in the inflammation occurs before the acne improves. When encapsulated within CPR 2001, the inflammatory action of the retinoic acid is significantly reduced.

A parallel set of experiments was conducted to test the efficacy of retinoic acid to inhibit the growth of psoriatic-type keratinocytes (PAM-212 cells) when the retinoic acid was incorporated into CPR 2001 liposomes. Here, separate groups of PAM-212 cells were exposed to either retinoic acid or retinoic acid encapsulated within CPR 2001 liposomes. Encapsulating retinoic acid within CPR 2001 liposomes had no effect on the activity of the retinoic acid to inhibit cell proliferation of PAM-212 cells.

In a second set of experiments, the anti-inflammatory activity of CPR 2001 was compared to that of 5-fluorouracil. The PMA-induced assay described above was followed.

In dermatology, 5-fluorouracil (5-FU) is used topically to treat actinic keratinosis, a premalignant skin condition caused by excessive exposure to the sun. Like retinoic acid, when 5-FU is applied to the skin it also causes a primary inflammatory response prior to reversing the actinic keratinosis. When applied topically to the ear of the mouse, 5-FU increases the inflammatory response due to PMA.

In the second set of experiments, vehicle alone, a 1% solution of dexamethasone, a 5% solution of CPR 2001, a 1% solution of 5-FU, and a formulation of 5-FU (1%) encapsulated within CPR 2001 liposomes (5% CPR 2001 overall), were applied to the ears of separate groups of PMA-induced mice. The results are as follows:

TABLE 3C

|  | % increase in ear weight |
|---|---|
| Vehicle only | 102 |
| 1% Dexamethasone | −1 |
| 5% CPR 2001 | 6 |
| 1% 5-FU | 150 |
| CPR 2001 + 5-FU | 5 |

By encapsulating 5-FU within liposomes of CPR 2001, the inflammatory response to the 5-FU in the test animals was reduced from 150% increase in ear weight to 5% increase in ear weight.

Again, a parallel set of experiments is conducted to test the efficacy of 5-FU to inhibit the growth of psoriatic-type keratinocytes (PAM-212 cells) when the 5-FU is incorporated into CPR 2001 liposomes. Separate groups of PAM-212 cells are exposed to either 5-FU or 5-FU encapsulated within CPR 2001 liposomes. Encapsulating 5-FU within CPR 2001 liposomes had no effect on the activity of the 5-FU to inhibit cell proliferation of PAM-212 cells.

These results demonstrate: 1) that CPR 2001 is an effective anti-inflammatory agent; and 2) that the inflammatory activity of medicinal compounds can be reduced, without adversely affecting the beneficial biological activity of the compounds, by incorporating them into liposomes containing CPR 2001 as a structural element.

EXAMPLE 4

Anti-PAF Activity

The following is a protocol for the evaluation of anti-PAF activity in anesthetized guinea pigs.

1. Guinea pigs of 650–1000 g are used to facilitate catheterization of the jugular vein and carotid artery. The guinea pigs are anesthetized with 35–45 mg/kg pentobarbital sodium. When or if the recordings are unstable, anesthetic additions are made during the course of the intervention. The cutdown is a ventral medial incision over the cervical area so that the trachea, jugular vein and carotid artery can be cannulated. The animals are immediately attached to a volume regulated Harvard® rodent respirator, Model 683, via a tracheostomy and the respirator is set at 60 respirations per minute and a volume of 8 ml/kg to maintain a normal arterial P—$CO_2$ of approximately 40 mmHg. Pancuronium, a muscle relaxant, is then given IV at a dose of 0.2 mg/kg to prevent spontaneous breathing. A tube is connected to the respirator pump and the endotracheal catheter is attached to a pressure transducing strain gauge and then to a 2-channel Gilson® physiological recorder. One channel of the recorder inscribes the pressure tracing from the airway; the second channel inscribes the pressure tracing from a similar strain gauge attached directly to a catheter inserted into the carotid artery. These two parameters are measured before and after each drug is given and at each increment in the dose response studies with each drug candidate and recorded. Total pulmonary resistance (TPR) is calculated as the difference between the expiratory pressure and inspiratory pressures with a constant volume.

After the anesthetic and muscle relaxant are given, the animal is allowed to stabilize. The airway is gently suctioned with a syringe, and the lungs are briefly inflated by closing the expiratory port on the ventilator until the pressure is approximately three times resting pressure. When the pressure returns to a steady state, this TPR is considered control pressure. The dose-related increases or decreases are quantitated against these controls to determine the percent inhibition of PAF activity. Two doses of PAF are given as controls before compound is administered.

Results:

PAF and incremental doses of 1, 3, 10, 30 and 50 $\mu$M per kg of CPR-2001 change the PAF-induced increase in TPR in all animals (m) as seen from the results in Table 4. Decreases of TPR in a dose-related way indicate an inhibition of the constrictor activity of PAF on the airway.

TABLE 4

|  | % of Controls | m |
|---|---|---|
| PAF Controls | 183.36 | 4 |
| CPR-2001 ($\mu$M/kg i.v.) |  |  |
| 1 | 193.75 | 1 |
| 3 | 124.58 | 3 |
| 10 | 98.19 | 4 |
| 30 | 19.60 | 3 |
| 50 | 8.33 | 1 |

EXAMPLE 5

Pharmaceutical Compositions

The following illustrative pharmaceutical compositions, containing CPR-2001 or a pharmaceutically acceptable salt thereof as the active ingredient, are each prepared according to art recognized methodologies in pharmacy.

A. Injectable:

| Component | Amount per Ampoule |
|---|---|
| Active Ingredient | 10.0 mg |
| Buffering Agent | — |
| Water, q.s. | 1.0 ml |

The active ingredient is dissolved in the water and the pH is adjusted to the proper value by the buffering agent. The solution is filtered and sterilized by autoclaving before being sealed under sterile conditions in ampoules.

B. Capsule

| Component | Amount per Capsule |
|---|---|
| Active Ingredient | 50 mg |
| Lactose | 450 mg |
| Magnesium Stearate | 5 mg |

The components are thoroughly mixed and then packed into a two-part gelatin capsule.

C. Tablet:

| Component | Amount per Tablet |
|---|---|
| Active Ingredient | 75.0 mg |
| Lactose | 110.0 mg |
| Corn starch, pregelatinized | 2.5 mg |
| Potato starch | 12.0 mg |
| Magnesium stearate | 0.5 mg |

The powdered components are intimately mixed and then compressed to afford a tablet.

D. Inhalation Cartridge:

| Component | Amount per Cartridge |
|---|---|
| Active ingredient, (10–50 microns) | 5.0 mg |
| Lactose, q.s. | 25.0 mg |

The active ingredient, premicronized to a fine particle size between 1–10 $\mu$m in diameter, is blended with normal tabletting grade lactose in a high energy mixer. The powder blend is filled into appropriately sized hard gelatin capsules on a suitable encapsulating machine. The contents of the cartridges are administered using a powder inhaler.

E. Oral Syrup:

| Component | % |
|---|---|
| Active ingredient | 10 w/v |
| Sorbitol solution, USP | 60 v/v |
| Flavoring agent, as required |  |
| Distilled water, q.s. | 100 |

The active ingredient is dissolved in some of the water with stirring. The sorbitol solution, flavoring agent and the rest of the water are added. The syrup is clarified by filtration through suitable cellulosic filter pads.

| F. Ointment: | |
| --- | --- |
| Component | % by Weight |
| Active ingredient (liposome) | 5 |
| Plasticized Hydrocarbon Gel | 100 |

The active ingredient, finely sieved, is uniformly blended with the plasticized hydrocarbon gel, commercially available as Plastibasee, a polyethylene and mineral oil gel base.

EXAMPLE 6

Liposome Formation

Five micromoles of CPR-2001 are dissolved in about 1 ml of chloroform. The solution is transferred to a 16×120 mm screw-capped tube. The tube is placed, uncapped, inside a 1×8 inch boiling tube with B24/40 standard glass fitting. Inside the boiling tube, in the space between the boiling tube and the smaller screwcapped tube, there is a small amount of distilled water to aid thermal contact between the inner and outer tube.

The boiling tube is placed on a rotary evaporator under reduced pressure to evaporate the chloroform and leave the lipid as a thin film in the lower portion of the screw-capped tube. The boiling tube is partly immersed in a water bath at 37° C. during the evaporation to aid the process.

Once a thin film has been formed, the screw-capped tube is removed from the boiling tube, and one ml of aqueous solution is added to it. The tube is capped and immersed in a water bath at 75° C. to aid swelling of the lipid. Swelling of the film is observed to occur when the film becomes cloudy, and is, with agitation, dislodged from the walls of the tube to give a cloudy suspension in the aqueous medium. This suspension is found to consist of liposomes by the application of two techniques. First, laser-light scattering, or QELS, reveal the presence of particles of 658 nm in diameter in one determination, 1468 nm in another. Second, electron microscopy shows that these particles have the characteristic concentric lamellar structure of liposomes.

In a second preparation, 10 micromoles of CPR 2001 are taken through the identical procedure described above. The material, being more concentrated in the final aqueous suspension, is found to be quite viscous. The particle size by QELS is greater than 5,000 nm. The material is then subjected to disruption to reduce the particle size by the following method. A cylindrical sonic bath, obtained from Laboratory Supplies Company, Hicksville, N.Y., is filled with warm distilled water at 75° C. The capped tube containing the suspension of CPR 2001 is immersed in the bath to a depth of no more than 2 cm. The tube is positioned at the center of the bath and suspended in a small clamp and ringstand assembly. The bath is switched on and the exact position of the tube, and the level of water in the bath, are adjusted to achieve maximum agitation of the tubels contents. After the initial "tuning" step, the bath is left to sonicate the sample for about 10 minutes. The solution becomes less turbid and viscous, and QELS reveal a particle size of the liposomes of 102 nm. Electron microscopy of the liposomes show that the particles are still multilamellar, but smaller.

Liposomes of the hydrogen iodide acid addition salt of α-tocopherylphosphocholine are obtained by following the foregoing procedures.

What is claimed is:

1. A pharmaceutical composition comprising an antiviral-effective, antifungal-effective, anti-inflammatory-effective, platelet-activating factor antagonist-effective, or ultra-violet radiation-blocking amount of a liposome of α-tocopherylphosphocholine or a liposome of a pharmaceutically-acceptable salt thereof, wherein the liposome comprises α-tocopherylphosphocholine or a pharmaceutically-acceptable salt thereof as its main structural component, wherein the amount ranges from about 0.5 to about 500 mg per unit dosage form, in combination with a pharmaceutically-acceptable carrier.

2. The composition of claim 1, wherein the pharmaceutically acceptable carrier comprises a carrier suitable for oral administration as a tablet or capsule.

3. The composition of claim 1, wherein the pharmaceutically acceptable carrier comprises a carrier suitable for inhalation administration.

4. The composition of claim 1, wherein the pharmaceutically acceptable carrier comprises a carrier in liquid form suitable for oral administration.

5. The composition of claim 1, wherein the pharmaceutically acceptable carrier comprises a carrier in liquid form suitable for parenteral administration.

6. The composition of claim 1, wherein the pharmaceutically acceptable carrier comprises a carrier suitable for topical application.

7. The composition of claim 1 in unit dosage form as a tablet or capsule containing α-tocopherylphosphocholine or a pharmaceutically acceptable salt thereof.

8. A liposome consisting of α-tocopherylphosphocholine or a salt thereof as its main structural component.

9. The liposome of claim 8, wherein the main structural component is a pharmaceutically-acceptable salt of α-tocopherylphosphocholine.

* * * * *